(12) United States Patent
Kawa

(10) Patent No.: US 10,507,177 B1
(45) Date of Patent: Dec. 17, 2019

(54) ANTI-AGING HAIR TREATMENT

(71) Applicant: Ino Beauty, Inc., Miami, FL (US)

(72) Inventor: Nour Kawa, Miami, FL (US)

( * ) Notice: Subject to any disclaimer, the term of this patent is extended or adjusted under 35 U.S.C. 154(b) by 0 days.

(21) Appl. No.: 16/394,390

(22) Filed: Apr. 25, 2019

Related U.S. Application Data

(63) Continuation-in-part of application No. 15/096,247, filed on Apr. 11, 2016, now Pat. No. 10,278,915.

(51) Int. Cl.
| | | |
|---|---|---|
| *A61K 36/52* | (2006.01) | |
| *A61K 36/48* | (2006.01) | |
| *A61K 36/889* | (2006.01) | |
| *A61K 36/539* | (2006.01) | |
| *A61K 8/97* | (2017.01) | |
| *A61Q 5/00* | (2006.01) | |
| *A61Q 5/02* | (2006.01) | |
| *A61Q 7/00* | (2006.01) | |
| *A61K 8/60* | (2006.01) | |
| *A61Q 5/12* | (2006.01) | |

(52) U.S. Cl.
CPC .............. *A61K 8/97* (2013.01); *A61Q 5/002* (2013.01); *A61Q 5/02* (2013.01); *A61Q 7/00* (2013.01); *A61K 8/60* (2013.01); *A61K 2800/5922* (2013.01); *A61Q 5/12* (2013.01)

(58) Field of Classification Search
CPC ...... A61K 36/52; A61K 36/48; A61K 36/889; A61K 36/539
USPC ................. 424/70.1, 74, 736, 741, 757, 727
See application file for complete search history.

(56) References Cited

U.S. PATENT DOCUMENTS

| | | |
|---|---|---|
| 7,989,599 B2 | 8/2011 | Suzuki et al. |
| 2009/0068255 A1* | 3/2009 | Yu ........................ A61K 8/0212 424/450 |

* cited by examiner

*Primary Examiner* — Michael Barker
*Assistant Examiner* — Deborah A Davis
(74) *Attorney, Agent, or Firm* — Sanchelima & Associates, P.A.; Christian Sanchelima; Jesus Sanchelima

(57) ABSTRACT

A hair strengthening, nourishment, and growth composition and method of application that can be used in the form of a shampoo.

6 Claims, No Drawings

ANTI-AGING HAIR TREATMENT

OTHER RELATED APPLICATIONS

The present application is a continuation-in-part and claims the benefit of the priority date of U.S. non provisional patent application Ser. No. 15/096,247 filed on Apr. 11, 2016, which is hereby incorporated by reference.

BACKGROUND OF THE INVENTION

Field of the Invention

The present invention relates to a hair, follicle and scalp composition and application method and, more particularly, to a composition that can be applied in a shampoo for stimulating hair follicles and neutralizing the scalp to stimulate longer, stronger, healthier, fuller looking hair. The composition strengthens and nurtures existing hair and many experience the appearance of fullness, thickness and growth.

Description of the Related Art

Several compositions for hair treatments have been designed in the past. None of them, however, include a composition that focuses on the health of the scalp, neutralizing the PH levels, providing the necessary ingredients to stimulate growth topically and to penetrate deeper into the scalp, while providing ingredients the stimulate blood vessels, provide protein and plant based nourishment and minimize inflammation.

Applicant believes that a related reference corresponds to U.S. Pat. No. 7,989,599 issued to National Institute of Advanced Ind Science and Tech AIST Toyo Boseki KK for an activator including biosurfactant as active ingredient, mannosyl erythritol lipid, and production method thereof.

However, it differs from the present invention because it does not teach or motivate one of ordinary skill in the art to combine the ingredients and combinations of the present formulation to provide as effective of a composition to promote the anti-aging of hair.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a composition that increases healing and suppresses free radical development on the skin and/or scalp of the user.

It is another object of this invention to provide a composition that repairs and prevents ultraviolet damage, damage caused by excessive styling or chemical treatments.

It is another object of this invention to enhance the shine of a user's hair.

It is still another object of the present invention to provide moisture and nourishment to the hair.

It is yet another object of the present invention to provide stimulation to the hair follicles.

It is still another object of the present invention to stabilize the PH level of a user's scalp.

It is another object of the present invention to boost proteins linked to stem cell functions to promote hair growth.

It is still another object of the present invention to reduce split ends.

It is another object of the present invention to promote blood flow to the scalp.

It is yet another object of the present invention to facilitate the communication of cells. It is yet another object of the invention to minimize the detrimental hair loss effects of Dihydrotestoterone.

It is still another object of the present invention to induce anti-inflammatory effects.

It is another object of the invention to prolong the life of existing hair.

It is another object of the invention to prevent excessive shedding, hair loss, increase hair density and volume, and activate dermal papilla cells.

The present invention can help hair look thicker, fuller, healthier and stronger than existing products on the market. Namely, it works by stimulating the hair follicle in various stages on the surface, i.e. wake it up.

It also has ingredients that: promote more circulation, blood flow and larger blood vessels; penetrate deeper into the scalp and signal the follicle to grow healthy; counter inflammation; provide balance; nourish the follicle, scalp and hair; balance hormonal disruption; and calm inflammation.

The state of the art includes compositions that are not focused on the scalp health and growth. They are focused on forcing the hair follicle to get back in its active stage, e.g. Rogain®, Nioxin®. There are other options that focus on stimulating the hair follicle.

The present invention focuses on the health of the scalp, neutralizing the PH levels, providing the necessary ingredients to stimulate growth topically and deeper into the scalp. The present invention provides these benefits while including ingredients that provide moisture, nourishment and support.

It is yet another object of this invention to provide such a composition that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

The composition can be included in a shampoo. This shampoo also works synergistically with the conditioner and serum. It helps prepare the hair to receive the conditioner and serum.

The core ingredients of the shampoo include:
a. Acetyl Cysteine;
b. Alcohol;
c. Inositol;
d. Lactose;
e. Citric acid;
f. Milk Protein (Lactis Proteinum);
g. Panthenyl Ethyl Ether;
h. *Serenoa;*
i. Sodium Citrate;
j. *Glycine soja* (soybean) Germ Extra;
k. Biotinoyl Tripeptide
l. Oleanolic Acid;
m. Butylene Glycol;
n. PEG-40 Hydrogenated Castor Oil;
o. PPG-26-Buteth-26;

p. Arginine;
q. Lactic Acid;
r. Propanediol;
s. *Scutellaria baicalensis* Root Extract;
t. Acetyl Methione;
u. *Triticum vulgare* (wheat) Germ Extract;
v. Beeswax;
w. Behenyl Alcohol;
x. *Butyrospermum parkii* (Shea Butter) Extract;
y. Ethylhexylglycerin;
z. Hydroxyethyl Behenamidopropyl Dimonium Chloride;
aa. Phenoxyethanol;
bb. *Pyrus malus* Extract;
cc. Caprylhydroxamic Acid;
dd. Caprylyl Glycol;
ee. Glycerin;
ff. Cetyl Betaine;
gg. *Citrullus colocynthis* Fruit Extract;
hh. *Pisum sativum* (Pea) Peptide;
ii. Cocamidopropyl Betaine;
jj. Sodium Cocoyl Isethionate;
kk. Sodium;
ll. *Cuscuta reflexa* (Giant Dodder) Extract;
mm. *Eclipta alba* Extract;
nn. Hydrolyzed *Quinoa;*
oo. Hydrolyzed Rice Protein;
pp. *Serrulata* Fruit Extract;
qq. Polyquaternium 7;
rr. Purified Water;
ss. Apigenin;
tt. Sodium Lauroyl Methyl Isethionate by weight;
uu. Stearamidopropyl Dimethylamine;
vv. *Leuconostoc*/Radish Root Ferment Filtrate;
ww. Cannabidiol (CBD);
xx. *Calendula officinalis* Flower Extract;
yy. *Citrus aurantium bergamia* (Bergamot) Fruit Extract;
zz. *Citrus grandis* (Grapefruit) Fruit Extract;
aaa. *Citrus limon* (Lemon) Peel Extract;
bbb. *Juniperus* Virginia Wood Extract;
ccc. *Santalum album* (Sandalwood) Wood Extract; and
ddd. *Vanilla planifolia* Fruit Extract.

The shampoo composition prevents accelerated hair loss with milk based bioactive signaling molecules using sulfur-rich amino acids. Also, this composition activates the stem cells by focusing on the surrounding connecting tissue. This composition also increases hair thickness and prevents functional disorders of the scalp and follicle cells.

Amodimethicone, C11-15 Pareth-7, Laureth-9, Trideceth-12 is a Paraben-free system and is used for the purposes of detangling.

Apigenin, lead to stimulation of follicle cell metabolism and lead to the slowdown of hair loss.

*Scutellaria baicalensis* Root Extract, *Triticum vulgare* (wheat) Germ Extract. This combination stimulates hair growth and stimulates hair stem cells. It lengthens the anogen hair cycle while shortening the telogen (or hair death) cycle. Helps actually change a hair from the telogen hair cycle to the anogen hair cycle. Provides additional sugars to the follicles which helps increase cellular respiration. Increases ATP production required for hair growth, development and maintenance. Protects against oxidative stress by microchondria stimulation.

Beeswax, *Butyrospermum parkii* (Shea Butter) Extract, *Pyrus malus* Extract promotes hair growth.

Citric Acid is used as a natural preservative and PH adjuster.

*Citrullus colocynthis* Fruit Extra and *Pisum sativum* (Pea) Peptide stimulate hair growth, nourishes and moisturizes the hair follicle; Hydrolyzed *Quinoa* provides hair repair and protection—substantively and penetration. Provides gloss and shine enhancement, hair color protection, and curl definition.

Hydrolyzed Rice Protein increases the volume of the hair shaft.

*Leuconostoc*/Radish Root Ferment Filtrate and *Serrulata* Fruit Extract stimulate hair growth, nourishes and moisturizes the hair follicle. Panthenyl Hydroxypropyl Steardimonium Chloride functions as an aesthetic, moisturizes and prevents fly aways. Polyquaternium 7 that reduces static and prevents fly away.

The composition can also be effectively implemented in the following ranges by percent by weight in a shampoo comprising:
a. approximately 0.5-8% Acetyl Cysteine by weight;
b. approximately 0.5-8% Acetyl Methione by weight;
c. approximately 0.5-8% Alcohol by weight;
d. approximately 0.5-8% Citric acid by weight;
e. approximately 0.5-8% Inositol by weight;
f. approximately 0.5-8% Lactose by weight;
g. approximately 0.5-8% Milk Protein (Lactis Proteinum) by weight;
h. approximately 0.5-8% Panthenyl Ethyl Ether by weight;
i. approximately 0.5-8% Sodium Citrate by weight;
j. approximately 0.1-18% Apigenin by weight;
k. approximately 0.1-18% Biotinoyl Tripeptide by weight;
l. approximately 0.1-18% Butylene Glycol by weight;
m. approximately 0.1-18% Oleanolic Acid by weight;
n. approximately 0.1-18% PEG-40 Hydrogenated Castor Oil by weight;
o. approximately 0.1-18% PPG-26-Buteth-26 by weight;
p. approximately 0.15-10% Arginine;
q. approximately 0.15-10% *Glycine soja* (soybean) Germ Extract by weight;
r. approximately 0.15-10% Lactic Acid by weight;
s. approximately 0.15-10% Propanediol by weight;
t. approximately 0.15-10% *Scutellaria baicalensis* Root Extract by weight;
u. approximately 0.15-10% *Triticum vulgare* (wheat) Germ Extract by weight;
v. approximately 0.01-8% Beeswax by weight;
w. approximately 0.01-8% Behenyl Alcohol by weight;
x. approximately 0.01-8% *Butyrospermum parkii* (Shea Butter) Extract by weight;
y. approximately 0.01-8% Ethylhexylglycerin by weight;
z. approximately 0.01-8% Hydroxyethyl Behenamidopropyl Dimonium Chloride by weight;
aa. approximately 0.01-8% Phenoxyethanol by weight;
bb. approximately 0.01-8% *Pyrus malus* Extract by weight;
cc. approximately 0.005-8% Caprylhydroxamic Acid by weight;
dd. approximately 0.005-8% Caprylyl Glycol by weight;
ee. approximately 0.005-8% Glycerin by weight;
ff. approximately 1-23% Cetyl Betaine by weight;
gg. approximately 0.0001-7% *Citrullus colocynthis* Fruit Extract by weight;
hh. approximately 0.0001-7% *Pisum sativum* (Pea) Peptide by weight;
ii. approximately 0.0001-7% *Serenoa* by weight;
jj. approximately 1-50% Cocamidopropyl Betaine;

kk. approximately 1-50% Sodium Cocoyl Isethionate by weight;
ll. approximately 1-50% Sodium Lauroyl Methyl Isethionate by weight;
mm. approximately 1-50% Sodium by weight;
nn. approximately 0.0001-7% *Cuscuta reflexa* (Giant Dodder) Extract by weight;
oo. approximately 0.0001-7% *Eclipta alba* Extract by weight;
pp. approximately 0.01-7% Hydrolyzed *Quinoa* by weight;
qq. approximately 0.01-8% Hydrolyzed Rice Protein by weight;
rr. approximately 0.0001-7% *Leuconostoc*/Radish Root Ferment Filtrate by weight;
ss. approximately 0.0001-7% *Serrulata* Fruit Extract by weight;
tt. approximately 0.2-5% Polyquaternium 7 by weight;
uu. approximately 1-60% Purified Water by weight;
vv. approximately 0.1-4% Stearamidopropyl Dimethylamine by weight;
ww. approximately 0-20% Cannabidiol (CBD) by weight;
xx. approximately 0-20% *Calendula officinalis* Flower Extract by weight;
yy. approximately 0-20% *Citrus aurantium bergamia* (Bergamot) Fruit Extract by weight;
zz. approximately 0-20% *Citrus grandis* (Grapefruit) Fruit Extract by weight;
aaa. approximately 0-20% *Citrus limon* (Lemon) Peel Extract by weight;
bbb. approximately 0-20% *Juniperus* Virginia Wood Extract by weight;
ccc. approximately 0-20% *Santalum album* (Sandalwood) Wood Extract by weight; and
ddd. approximately 0-20% *Vanilla planifolia* Fruit Extract by weight.

The composition can also be effectively implemented in the following ranges by percent by weight in one embodiment of the shampoo comprising:
a. approximately 1-4% Acetyl Cysteine by weight;
b. approximately 1-4% Acetyl Methione by weight;
c. approximately 1-4% Alcohol by weight;
d. approximately 1-4% Inositol by weight;
e. approximately 1-4% Lactose by weight;
f. approximately 1-4% Milk Protein (Lactis Proteinum) by weight;
g. approximately 1-4% Panthenyl Ethyl Ether by weight;
h. approximately 1-4% Sodium Citrate by weight;
i. approximately 0.5-6% Apigenin by weight;
j. approximately 0.5-6% Biotinoyl Tripeptide by weight;
k. approximately 0.5-6% Butylene Glycol by weight;
l. approximately 0.5-6% Oleanolic Acid by weight;
m. approximately 0.5-6% PEG-40 Hydrogenated Castor Oil by weight;
n. approximately 0.5-6% PPG-26-Buteth-26 by weight;
o. approximately 0.5-3% Arginine by weight;
p. approximately 0.5-3% *Glycine soja* (soybean) Germ Extract by weight;
q. approximately 0.5-3% Lactic Acid by weight;
r. approximately 0.5-3% Propanediol by weight;
s. approximately 0.5-3% *Scutellaria baicalensis* Root Extract by weight;
t. approximately 0.5-3% *Triticum vulgare* (wheat) Germ Extract by weight;
u. approximately 0.1-4% Beeswax by weight;
v. approximately 0.1-4% Behenyl Alcohol by weight;
w. approximately 0.1-4% *Butyrospermum parkii* (Shea Butter) Extract by weight;
x. approximately 0.1-4% Ethylhexylglycerin by weight;
y. approximately 0.1-4% Hydroxyethyl Behenamidopropyl Dimonium Chloride (by weight;
z. approximately 0.1-4% Phenoxyethanol by weight;
aa. approximately 0.1-4% *Pyrus malus* Extract by weight;
bb. approximately 0.005-4% Caprylhydroxamic Acid by weight;
cc. approximately 0.005-4% Caprylyl Glycol by weight;
dd. approximately 0.005-4% Glycerin by weight;
ee. approximately 2-12% Cetyl Betaine by weight;
ff. approximately 0.001-4% Citric Acid by weight;
gg. approximately 0.0001-7% *Citrullus colocynthis* Fruit Extract by weight;
hh. approximately 0.0001-7% *Pisum sativum* (Pea) Peptide by weight;
ii. approximately 0.0001-7% *Serenoa* by weight;
jj. approximately 18-41% Cocamidopropyl Betaine by weight;
kk. approximately 18-41% Sodium Cocoyl Isethionate by weight;
ll. approximately 18-41% Sodium Lauroyl Methyl Isethionate by weight;
mm. approximately 18-41% Sodium by weight;
nn. approximately 0.1-3% *Cuscuta reflexa* (Giant Dodder) Extract by weight;
oo. approximately 0.1-3% *Eclipta alba* Extract by weight;
pp. approximately 1-5% Hydrolyzed *Quinoa* by weight;
qq. approximately 0.01-5% Hydrolyzed Rice Protein by weight;
rr. approximately 0.0001-7% *Leuconostoc*/Radish Root Ferment Filtrate by weight;
ss. approximately 0.0001-7% *Serrulata* Fruit Extract by weight;
tt. approximately 1-4% Polyquaternium 7 by weight;
uu. approximately 1-60% Purified Water by weight;
vv. approximately 0.5-3% Stearamidopropyl Dimethylamine by weight;
ww. approximately 0-20% Cannabidiol (CBD) by weight;
xx. approximately 0-20% *Calendula officinalis* Flower Extract by weight;
yy. approximately 0-20% *Citrus aurantium bergamia* (Bergamot) Fruit Extract by weight;
zz. approximately 0-20% *Citrus grandis* (Grapefruit) Fruit Extract by weight;
aaa. approximately 0-20% *Citrus limon* (Lemon) Peel Extract by weight;
bbb. approximately 0-20% *Juniperus* Virginia Wood Extract by weight;
ccc. approximately 0-20% *Santalum album* (Sandalwood) Wood Extract by weight and
ddd. approximately 0-20% *Vanilla planifolia* Fruit Extract by weight.

The core and secondary ingredients of the shampoo include:
a. Acetyl Cysteine;
b. Acetyl Methione;
c. Alcohol;
d. Citric acid;
e. Inositol;
f. Lactose;
g. Milk Protein (Lactis Proteinum);
h. Panthenyl Ethyl Ether;
i. Sodium Citrate;
j. Acrylates/C10-30 Alkyl Acrylates Crosspolymer;
k. Amodimethicone;

l. C11-15 Pareth-7;
m. Laureth-9;
n. Trideceth-12;
o. Apigenin;
p. Biotinoyl Tripeptide;
q. Butylene Glycol;
r. Oleanolic Acid;
s. PEG-40 Hydrogenated Castor Oil;
t. PPG-26-Buteth-26;
u. Arginine;
v. *Glycine soja* (soybean) Germ Extract;
w. Lactic Acid;
x. Propanediol;
y. *Scutellaria baicalensis* Root Extract;
z. *Triticum vulgare* (wheat) Germ Extract;
aa. Beeswax;
bb. Behenyl Alcohol;
cc. *Butyrospermum parkii* (Shea Butter) Extract;
dd. Ethylhexylglycerin;
ee. Hydroxyethyl Behenamidopropyl Dimonium Chloride;
ff. Phenoxyethanol;
gg. *Pyrus malus* Extract;
hh. *Camellia sinensis* Leaf Extract;
ii. Caprylic/Capric Triglyceride;
jj. *Coffea arabica* (Coffee) Leaf/Seed Extract;
kk. *Cucumis melo cantalupensis* Fruit Extract;
ll. *Eugenia caryophyllus* (Clove) Flower Extract;
mm. *Elettaria cardamomum* Seed Extract;
nn. *Jasminum officinale* (Jasmine) Flower/Leaf Extract;
oo. *Pyrus malus* Apple Fruit Extract;
pp. *Rosa damascena* Flower Extract;
qq. *Rubus fruticosus* (Blackberry) Fruit Extract;
rr. Caprylhydroxamic Acid;
ss. Caprylyl Glycol;
tt. Glycerin;
uu. Cetyl Betaine;
vv. *Citrullus colocynthis* Fruit Extract;
ww. *Pisum sativum* (Pea) Peptide (and) *Serenoa;*
xx. Glycol Distearate;
yy. Laureth-4;
zz. Cocamidopropyl Betaine;
aaa. Sodium Cocoyl Isethionate;
bbb. Sodium;
ccc. *Cuscuta reflexa* (Giant Dodder) Extract;
ddd. *Eclipta alba* Extract;
eee. Guar Hydroxypropyltrimonium Chloride;
fff. Hydrolyzed *Quinoa;*
ggg. Hydrolyzed Rice Protein;
hhh. *Leuconostoc*/Radish Root Ferment Filtrate;
iii. *Serrulata* Fruit Extract;
jjj. Methyl Oleoyl Taurate;
kkk. Panthenyl Hydroxypropyl Steardimonium Chloride;
lll. Polyquaternium 7;
mmm. Purified Water;
nnn. Sodium Lauroyl Methyl Isethionate;
ooo. Stearamidopropyl Dimethylamine;
ppp. Cannabidiol (CBD);
qqq. *Calendula officinalis* Flower Extract;
rrr. *Citrus aurantium bergamia* (Bergamot) Fruit Extract;
sss. *Citrus grandis* (Grapefruit) Fruit Extract;
ttt. *Citrus limon* (Lemon) Peel Extract;
uuu. *Juniperus* Virginia Wood Extract;
vvv. *Santalum album* (Sandalwood) Wood Extract; and
www. *Vanilla planifolia* Fruit Extract.

The shampoo can be implemented with the following ranges:

a. approximately 0.5-8% Acetyl Cysteine by weight;
b. approximately 0.5-8% Acetyl Methione by weight;
c. approximately 0.5-8% Alcohol by weight;
d. approximately 0.5-8% Inositol by weight;
e. approximately 0.5-8% Lactose by weight;
f. approximately 0.5-8% Milk Protein (Lactis Proteinum) by weight;
g. approximately 0.5-8% Panthenyl Ethyl Ether by weight;
h. approximately 0.5-8% Sodium Citrate by weight; and
i. approximately 3-30% Acrylates/C10-30 Alkyl Acrylates Crosspolymer;
j. approximately 0.05-24% Amodimethicone by weight;
k. approximately 0.05-24% C11-15 Pareth-7 by weight;
l. approximately 0.0001-24% Glycerin by weight;
m. approximately 0.05-24% Laureth-9 by weight;
n. approximately 0.05-24% Trideceth-12 Paraben-free by weight;
o. approximately 0.1-18% Apigenin by weight;
p. approximately 0.1-18% Biotinoyl Tripeptide by weight;
q. approximately 0.1-18% Butylene Glycol by weight;
r. approximately 0.1-18% Oleanolic Acid by weight;
s. approximately 0.1-18% PEG-40 Hydrogenated Castor Oil by weight;
t. approximately 0.1-18% PPG-26-Buteth-26 by weight;
u. approximately 0.15-10% Arginine by weight;
v. approximately 0.15-10% *Glycine soja* (soybean) Germ Extract by weight;
w. approximately 0.15-10% Lactic Acid by weight;
x. approximately 0.15-10% Propanediol by weight;
y. approximately 0.15-10% *Scutellaria baicalensis* Root Extract by weight;
z. approximately 0.15-10% *Triticum vulgare* (wheat) Germ Extract by weight;
aa. approximately 0.01-8% Beeswax by weight;
bb. approximately 0.01-8% Behenyl Alcohol by weight;
cc. approximately 0.01-8% *Butyrospermum parkii* (Shea Butter) Extract by weight;
dd. approximately 0.01-8% Ethylhexylglycerin by weight;
ee. approximately 0.01-8% Hydroxyethyl Behenamidopropyl Dimonium Chloride by weight;
ff. approximately 0.01-8% Phenoxyethanol by weight;
gg. approximately 0.01-8% *Pyrus malus* Extract by weight;
hh. approximately 0.005-7% *Camellia sinensis* Leaf Extract by weight;
ii. approximately 0.005-7% Caprylic/Capric Triglyceride by weight;
jj. approximately 0.005-7% *Coffea arabica* (Coffee) Leaf/Seed Extract by weight;
kk. approximately 0.005-7% *Cucumis melo cantalupensis* Fruit Extract by weight;
ll. approximately 0.005-7% *Eugenia caryophyllus* (Clove) Flower Extract by weight;
mm. approximately 0.005-7% *Elettaria cardamomum* Seed Extract by weight;
nn. approximately 0.005-7% *Jasminum officinale* (Jasmine) Flower/Leaf Extract by weight;
oo. approximately 0.005-7% *Pyrus malus* Apple Fruit Extract by weight;
pp. approximately 0.005-7% *Rosa damascena* Flower Extract by weight;
qq. approximately 0.005-7% *Rubus fruticosus* (Blackberry) Fruit Extract by weight;

rr. approximately 0.005-8% Caprylhydroxamic Acid by weight;
ss. approximately 0.005-8% Caprylyl Glycol by weight;
tt. approximately 1-23% Cetyl Betaine by weight;
uu. approximately 0.001-8% Citric Acid by weight;
vv. approximately 0.0001-7% *Citrullus colocynthis* Fruit Extract;
ww. approximately 0.0001-7% *Pisum sativum* (Pea) Peptide;
xx. approximately 0.0001-7% *Serenoa* by weight;
yy. approximately 1-8% Glycol Distearate;
zz. approximately 1-8% Laureth-4 by weight;
aaa. approximately 1-50% Cocamidopropyl Betaine by weight;
bbb. approximately 1-50% Sodium Cocoyl Isethionate by weight;
ccc. approximately 1-50% Sodium Lauroyl Methyl Isethionate by weight;
ddd. approximately 1-50% Sodium by weight,
eee. approximately 1-50% Methyl Oleoyl Taurate by weight;
fff. approximately 0.0001-7% *Cuscuta reflexa* (Giant Dodder) Extract by weight;
ggg. approximately 0.0001-7% *Eclipta alba* Extract by weight;
hhh. approximately 0.01-5% Guar Hydroxypropyltrimonium Chloride by weight;
iii. approximately 0.01-7% Hydrolyzed *Quinoa* by weight;
jjj. approximately 0.01-8% Hydrolyzed Rice Protein by weight;
kkk. approximately 0.0001-7% *Leuconostoc*/Radish Root Ferment Filtrate by weight;
lll. approximately 0.0001-7% *Serrulata* Fruit Extract by weight;
mmm. approximately 0.001-8% Panthenyl Hydroxypropyl Steardimonium Chloride by weight;
nnn. approximately 0.2-5% Polyquaternium 7 by weight;
ooo. approximately 1-60% Purified Water by weight;
ppp. approximately 0.1-4% Stearamidopropyl Dimethylamine by weight;
qqq. approximately 0-20% Cannabidiol (CBD) by weight;
rrr. approximately 0-20% *Calendula officinalis* Flower Extract by weight;
sss. approximately 0-20% *Citrus aurantium bergamia* (Bergamot) Fruit Extract by weight;
ttt. approximately 0-20% *Citrus grandis* (Grapefruit) Fruit Extract by weight;
uuu. approximately 0-20% *Citrus limon* (Lemon) Peel Extract by weight;
vvv. approximately 0-20% *Juniperus* Virginia Wood Extract by weight;
www. approximately 0-20% *Santalum album* (Sandalwood) Wood Extract by weight; and
xxx. approximately 0-20% *Vanilla planifolia* Fruit Extract by weight.

In an alternate embodiment, the shampoo can be implemented using the following ranges:
a. approximately 1-4% Acetyl Cysteine by weight;
b. approximately 1-4% Acetyl Methione by weight;
c. approximately 1-4% Alcohol by weight;
d. approximately 1-4% Inositol by weight;
e. approximately 1-4% Lactose by weight;
f. approximately 1-4% Milk Protein (Lactis Proteinum) by weight;
g. approximately 1-4% Panthenyl Ethyl Ether by weight;
h. approximately 1-4% Sodium Citrate by weight;
i. approximately 4-20% Acrylates/C10-30 Alkyl Acrylates Crosspolymer;
j. approximately 1-15% Amodimethicone by weight;
k. approximately 1-15% C11-15 Pareth-7 by weight;
l. approximately 1-15% Laureth-9 by weight;
m. approximately 1-15% Trideceth-12 Paraben-free by weight;
n. approximately 0.5-6% Apigenin by weight;
o. approximately 0.5-6% Biotinoyl Tripeptide by weight;
p. approximately 0.5-6% Butylene Glycol by weight;
q. approximately 0.5-6% Oleanolic Acid by weight;
r. approximately 0.5-6% PEG-40 Hydrogenated Castor Oil by weight
s. approximately 0.5-6% PPG-26-Buteth-26 by weight;
t. approximately 0.5-3% Arginine;
u. approximately 0.5-3% *Glycine soja* (soybean) Germ Extract by weight;
v. approximately 0.5-3% Lactic Acid by weight;
w. approximately 0.5-3% Propanediol by weight;
x. approximately 0.5-3% *Scutellaria baicalensis* Root Extract by weight
y. approximately 0.5-3% *Triticum vulgare* (wheat) Germ Extract by weight;
z. approximately 0.1-4% Beeswax by weight;
aa. approximately 0.1-4% Behenyl Alcohol by weight;
bb. approximately 0.1-4% *Butyrospermum parkii* (Shea Butter) Extract by weight;
cc. approximately 0.1-4% Ethylhexylglycerin by weight;
dd. approximately 0.1-4% Hydroxyethyl Behenamidopropyl Dimonium Chloride by weight;
ee. approximately 0.1-4% Phenoxyethanol by weight;
ff. approximately 0.1-4% *Pyrus malus* Extract by weight;
gg. approximately 0.005-3% *Camellia sinensis* Leaf Extract by weight;
hh. approximately 0.005-3% Caprylic/Capric Triglyceride by weight;
ii. approximately 0.005-3% *Coffea arabica* (Coffee) Leaf/Seed Extract by weight;
jj. approximately 0.005-3% *Cucumis melo cantalupensis* Fruit Extract by weight;
kk. approximately 0.005-3% *Eugenia caryophyllus* (Clove) Flower Extract by weight;
ll. approximately 0.005-3% *Elettaria cardamomum* Seed Extract by weight;
mm. approximately 0.005-3% *Jasminum officinale* (Jasmine) Flower/Leaf Extract (and) *Pyrus malus* Apple Fruit Extract by weight;
nn. approximately 0.005-3% *Rosa damascena* Flower Extract by weight;
oo. approximately 0.005-3% *Rubus fruticosus* (Blackberry) Fruit Extract by weight;
pp. approximately 0.005-4% Caprylhydroxamic Acid by weight;
qq. approximately 0.005-4% Caprylyl Glycol by weight;
rr. approximately 2-12% Cetyl Betaine by weight;
ss. approximately 0.001-4% Citric Acid by weight
tt. approximately 0.0001-7% *Citrullus colocynthis* Fruit Extract by weight;
uu. approximately 0.0001-7% *Pisum sativum* (Pea) Peptide by weight;
vv. approximately 0.0001-7% *Serenoa* by weight;
ww. approximately 1-5% Cocamidopropyl Betaine by weight;
xx. approximately 1-5% Glycol Distearate by weight;
yy. approximately 1-5% Laureth-4 by weight;

zz. approximately 18-41% Cocamidopropyl Betaine by weight;
aaa. approximately 18-41% Sodium Cocoyl Isethionate by weight;
bbb. approximately 18-41% Sodium Lauroyl Methyl Isethionate by weight;
ccc. approximately 18-41% Sodium by weight;
ddd. approximately 18-41% Methyl Oleoyl Taurate by weight;
eee. approximately 0.1-3% *Cuscuta reflexa* (Giant Dodder) Extract (and) *Eclipta alba* Extract by weight;
fff. approximately 0.1-15% Glycerin by weight;
ggg. approximately 0.01-3% Guar Hydroxypropyltrimonium Chloride by weight;
hhh. approximately 1-5% Hydrolyzed *Quinoa* by weight;
iii. approximately 0.01-5% Hydrolyzed Rice Protein by weight;
jjj. approximately 0.0001-7% *Leuconostoc*/Radish Root Ferment Filtrate by weight;
kkk. approximately 0.0001-7% *Serrulata* Fruit Extract by weight;
lll. approximately 0.1-4% Panthenyl Hydroxypropyl Steardimonium Chloride by weight;
mmm. approximately 1-4% Polyquaternium 7 by weight;
nnn. approximately 1-60% Purified Water by weight;
ooo. approximately 0.5-3% Stearamidopropyl Dimethylamine by weight;
ppp. approximately 0-20% Cannabidiol (CBD) by weight;
qqq. approximately 0-20% *Calendula officinalis* Flower Extract by weight;
rrr. approximately 0-20% *Citrus aurantium bergamia* (Bergamot) Fruit Extract by weight;
sss. approximately 0-20% *Citrus grandis* (Grapefruit) Fruit Extract by weight;
ttt. approximately 0-20% *Citrus limon* (Lemon) Peel Extract by weight;
uuu. approximately 0-20% *Juniperus* Virginia Wood Extract by weight;
vvv. approximately 0-20% *Santalum album* (Sandalwood) Wood Extract by weight; and
www. approximately 0-20% *Vanilla planifolia* Fruit Extract by weight.

The application of the shampoo is disclosed hereafter. The shampoo is applied on the scalp in a circular motion at the hair root and leave on for five minutes or longer. Can be used as desired, for optimal results use 3-5 times a week.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An anti-aging treatment shampoo comprising:
a. Acetyl Cysteine;
b. Alcohol;
c. Inositol;
d. Lactose;
e. Citric acid;
f. Milk Protein (Lactis Proteinum);
g. Panthenyl Ethyl Ether;
h. *Serenoa*;
i. Sodium Citrate;
j. *Glycine soja* (soybean) Germ Extract;
k. Biotinoyl Tripeptide;
l. Oleanolic Acid;
m. Butylene Glycol;
n. PEG-40 Hydrogenated Castor Oil;
o. PPG-26-Buteth-26;
p. Arginine
q. Lactic Acid
r. Propanediol
s. *Scutellaria baicalensis* Root Extract;
t. Acetyl Methione
u. *Triticum vulgare* (wheat) Germ Extract;
v. Beeswax;
w. Behenyl Alcohol
x. *Butyrospermum parkii* (Shea Butter) Extract
y. Ethylhexylglycerin
z. Hydroxyethyl Behenamidopropyl Dimonium Chloride
aa. Phenoxyethanol
bb. *Pyrus malus* Extract;
cc. Caprylhydroxamic Acid
dd. Caprylyl Glycol
ee. Glycerin;
ff. Cetyl Betaine;
gg. *Citrullus colocynthis* Fruit Extract
hh. *Pisum sativum* (Pea) Peptide;
ii. Cocamidopropyl Betaine
jj. Sodium Cocoyl Isethionate
kk. Sodium;
ll. *Cuscuta reflexa* (Giant Dodder) Extract;
mm. *Eclipta alba* Extract;
nn. Hydrolyzed *Quinoa*;
oo. Hydrolyzed Rice Protein;
pp. *Serrulata* Fruit Extract;
qq. Polyquatemium 7;
rr. Purified Water;
ss. Apigenin;
tt. Sodium Lauroyl Methyl Isethionate by weight;
uu. Stearamidopropyl Dimethylamine;
vv. *Leuconostoc*/Radish Root Ferment Filtrate;
ww. Cannabidiol (CBD);
xx. *Calendula officinalis* Flower Extract;
yy. *Citrus aurantium bergamia* (Bergamot) Fruit Extract;
zz. *Citrus grandis* (Grapefruit) Fruit Extract;
aaa. *Citrus* (*Limon*) Peel Extract
bbb. *Juniperus* Virginia Wood Extract;
ccc. *Santalum album* (Sandalwood) Wood Extract; and
ddd. *Vanilla planifolia* Fruit Extract.

2. The composition of claim 1 comprising:
a. approximately 0.5-8% Acetyl Cysteine by weight;
b. approximately 0.5-8% Alcohol by weight;
c. approximately 0.5-8% Inositol by weight;
d. approximately 0.5-8% Lactose by weight;
e. approximately 0.5-8% Citric acid by weight;
f. approximately 0.5-8% Milk Protein (Lactis Proteinum) by weight;
g. approximately 0.5-8% Panthenyl Ethyl Ether by weight;
h. approximately 0.0001-7% *Serenoa* by weight;
i. approximately 0.5-8% Sodium Citrate by weight;
j. approximately 0.15-10% *Glycine soja* (soybean) Germ Extract by weight;
k. approximately 0.1-18% Biotinoyl Tripeptide by weight;
l. approximately 0.1-18% Oleanolic Acid by weight;
m. approximately 0.1-18% Butylene Glycol by weight;
n. approximately 0.1-18% PEG-40 Hydrogenated Castor Oil by weight;
o. approximately 0.1-18% PPG-26-Buteth-26 by weight;
p. approximately 0.15-10% Arginine by weight;
q. approximately 0.15-10%0/Lactic Acid by weight;
r. approximately 0.15-10% Propanediol by weight;

s. approximately 0.15-10% *Scutellaria baicalensis* Root Extract by weight;
t. approximately 0.5-8% Acetyl Methione by weight;
u. approximately 0.15-10% *Triticum vulgare* (wheat) Germ Extract by weight;
v. approximately 0.01-8% Beeswax by weight;
w. approximately 0.01-8% Behenyl Alcohol by weight;
x. approximately 0.01-8% *Butyrospermum parkii* (Shea Butter) Extract by weight;
y. approximately 0.01-8% Ethylhexylglycerin by weight;
z. approximately 0.01-8% Hydroxy ethyl Behenamidopropyl Dimonium Chloride by weight;
aa. approximately 0.01-8% Phenoxyethanol by weight;
bb. approximately 0.01-8% *Pyrus malus* Extract by weight;
cc. approximately 0.005-8% Caprylhydroxamic Acid by weight;
dd. approximately 0.005-8% Caprylyl Glycol by weight;
ee. approximately 0.005-8% Glycerin by weight;
ff. approximately 1-23% Cetyl Betaine by weight;
gg. approximately 0.0001-7% *Citrullus colocynthis* Fruit Extract by weight;
hh. approximately 0.0001-7% *Pisum sativum* (Pea) Peptide by weight;
ii. approximately 1-50% Cocamidopropyl Betaine;
jj. approximately 1-50% Sodium Cocoyl Isethionate by weight;
kk. approximately 1-50% Sodium by weight;
ll. approximately 0.0001-7% *Cuscuta reflexa* (Giant Dodder) Extract by weight;
mm. approximately 0.0001-7% *Eclipta alba* Extract by weight;
nn. approximately 0.01-7% Hydrolyzed *Quinoa* by weight;
oo. approximately 0.01-8% Hydrolyzed Rice Protein by weight;
pp. approximately 0.0001-7% *Serrulata* Fruit Extract by weight;
qq. approximately 0.2-5% Polyquaternium 7 by weight;
rr. approximately 1-60% Purified Water by weight;
ss. approximately 1-18% Apigenin by weight;
tt. approximately 1-50% Sodium Lauroyl Methyl Isethionater by weight;
uu. approximately 0.1-4% Stearamidopropyl Dimethylamine by weight;
vv. approximately 0.0001-7% *Leuconostoc*/Radish Root Ferment Filtrate by weight;
ww. approximately 0-20% Cannabidiol (CBD) by weight;
xx. approximately 0-20% *Calendula officinalis* Flower Extract by weight;
yy. approximately 0-20% *Citrus aurantium bergamia* (Bergamot) Fruit Extract by weight;
zz. approximately 0-20% *Citrus grandis* (Grapefruit) Fruit Extract by weight;
aaa. approximately 0-20% *Citrus limon* (Lemon) Peel Extract by weight;
bbb. approximately 0-20% *Juniperus* Virginia Wood Extract by weight;
ccc. approximately 0-20% *Santalum album* (Sandalwood) Wood Extract by weight; and
ddd. approximately 0-20% *Vanilla planifolia* Fruit Extract by weight.

3. The composition of claim 1 comprising:
a. approximately 1-4% Acetyl Cysteine by weight;
b. approximately 1-4% Alcohol by weight;
c. approximately 1-4% Inositol by weight
d. approximately 1-4% Lactose by weight;
e. approximately 0.001-4% Citric Acid by weight;
f. approximately 1-4% Milk Protein (Lactis Proteinum) by weight;
g. approximately 1-4% Panthenyl Ethyl Ether by weight;
h. approximately 0.0001-7% *Serenoa* by weight;
i. approximately 1-4% Sodium Citrate by weight;
j. approximately 0.5-3% *Glycine soja* (soybean) Germ Extract by weight;
k. approximately 0.5-6% Biotinoyl Tripeptide by weight;
l. approximately 0.5-6% Oleanolic Acid by weight;
m. approximately 0.5-6% Butylene Glycol by weight;
n. approximately 0.5-6% PEG-40 Hydrogenated Castor Oil by weight;
o. approximately 0.5-6% PPG-26-Buteth-26 by weight;
p. approximately 0.5-3% Arginine by weight;
q. approximately 0.5-3% Lactic Acid by weight;
r. approximately 0.5-3% Propanediol by weight;
s. approximately 0.5-3% *Scutellaria baicalensis* Root Extract by weight;
t. approximately 1-4% Acetyl Methione by weight;
u. approximately 0.5-3% *Triticum vulgare* (wheat) Germ Extract by weight;
v. approximately 0.1-4% Beeswax by weight;
w. approximately 0.1-4% Behenyl Alcohol by weight;
x. approximately 0.1-4% *Butyrospermum parkii* (Shea Butter) Extract by weight;
y. approximately 0.1-4% Ethylhexylglycerin by weight;
z. approximately 0.1-4% Hydroxyethyl Behenamidopropyl Dimonium Chloride by weight;
ss. approximately 0.5-6% Apigenin by weight;
aa. approximately 0.1-4% Phenoxyethanol by weight;
bb. approximately 0.1-4% *Pyrus malus* Extract by weight;
cc. approximately 0.005-4% Caprylhydroxamic Acid by weight;
dd. approximately 0.005-4% Caprylyl Glycol by weight;
ee. approximately 0.005-4% Glycerin by weight;
ff. approximately 2-12% Cetyl Betaine by weight;
gg. approximately 0.0001-7% *Citrullus colocynthis* Fruit Extract by weight;
hh. approximately 0.0001-7% *Pisum sativum* (Pea) Peptide by weight;
ii. approximately 18-41% Cocamidopropyl Betaine by weight;
jj. approximately 18-41% Sodium Cocoyl Isethionate by weight;
kk. approximately 18-41% Sodium by weight;
ll. approximately 0.1-3% *Cuscuta reflexa* (Giant Dodder) Extract by weight;
mm. approximately 0.1-3% *Eclipta alba* Extract by weight;
nn. approximately 1-5% Hydrolyzed *Quinoa* by weight;
oo. approximately 0.01-5% Hydrolyzed Rice Protein by weight;
pp. approximately 0.0001-7% *Serrulata* Fruit Extract by weight;
qq. approximately 1-4% Polyquaternium 7 by weight;
rr. approximately 1-60% Purified Water by weight;
ss. approximately 0.5-6% Apigenin by weight;
tt. approximately 18-41% Sodium Lauroyl Methyl Isethionate by weight;
uu. approximately 0.5-3% Stearamidopropyl Dimethylamine by weight;
vv. approximately 0.0001-7% *Leuconostoc*/Radish Root Ferment Filtrate by weight;
ww. approximately 0-20% Cannabidiol (CBD) by weight;
xx. approximately 0-20% *Calendula officinalis* Flower Extract by weight;

yy. approximately 0-20% *Citrus aurantium bergamia* (Bergamot) Fruit Extract by weight;
zz. approximately 0-20% *Citrus grandis* (Grapefruit) Fruit Extract by weight;
aaa. approximately 0-20% *Citrus limon* (Lemon) Peel Extract by weight;
bbb. approximately 0-20% *Juniperus* Virginia Wood Extract by weight;
ccc. approximately 0-20% *Santalum album* (Sandalwood) Wood Extract by weight; and
ddd. approximately 0-20% *Vanilla planifolia* Fruit Extract by weight.

4. The anti-aging treatment shampoo subject of claim 1 further comprising:
aaaa. Acrylates/C10-30 Alkyl Acrylates Crosspolymer;
bbbb. Amodimethicone;
cccc. CI 1-15 Pareth-7;
dddd. Laureth-9;
eeee. Trideceth-12;
ffff. *Camellia sinensis* Leaf Extract;
gggg. Caprylic/Capric Triglyceride;
hhhh. *Coffea arabica* (Coffee) Leaf/Seed Extract;
iiii. *Cucumis melo cantalupensis* Fruit Extract;
jjjj. *Eugenia caryophyllus* (Clove) Flower Extract;
kkkk. *Elettaria cardamomum* Seed Extract;
llll. *Jasminum officinale* (Jasmine) Flower/Leaf Extract;
mmmm. *Rosa damascena* Flower Extract;
nnnn. *Rubus fruticosus* (Blackberry) Fruit Extract;
oooo. Glycol Di stearate;
pppp. Laureth-4;
qqqq. Guar Hydroxypropyltrimonium Chloride;
rrrr. Methyl Oleoyl Taurate;
ssss. Panthenyl Hydroxypropyl Steardimonium Chloride.

5. The composition of claim 4 comprising:
aaaa. approximately 3-30% Acrylates/Cl0-30 Alkyl Acrylates Crosspolymer;
bbbb. approximately 0.05-24% Amodimethicone by weight;
cccc. approximately 0.05-24% Cl 1-15 Pareth-7 by weight;
dddd. approximately 0.05-24% Laureth-9 by weight;
eeee. approximately 0.05-24% Trideceth-12 by weight;
ffff. approximately 0.005-7% *Camellia sinensis* Leaf Extract by weight
gggg. approximately 0.005-7% Caprylic/Capric Triglyceride by weight;
hhhh. approximately 0.005-7% *Coffea arabica* (Coffee) Leaf/Seed Extract by weight;
iiii. approximately 0.005-7% *Cucumis melo cantalupensis* Fruit Extract by weight;
jjjj. approximately 0.005-7% *Eugenia caryophyllus* (Clove) Flower Extract by weight;
kkkk. approximately 0.005-7% *Elettaria cardamomum* Seed Extract by weight;
llll. approximately 0.005-7% *Jasminum officinale* (Jasmine) Flower/Leaf Extract by weight;
mmmm. approximately 0.005-7% *Rosa damascena* Flower Extract by weight;
nnnn. approximately 0.005-7% *Rubus fruticosus* (Blackberry) Fruit Extract by weight;
oooo. approximately 1-8% Glycol Distearate;
pppp. approximately 1-8% Laureth-4 by weight;
qqqq. approximately 0.01-5% Guar Hydroxypropyltrimonium Chloride by weight;
rrrr. approximately 1-50% Methyl Oleoyl Taurate by weight;
ssss. approximately 0.001-8% Panthenyl Hydroxypropyl Steardimonium Chloride.

6. A method for treating the scalp comprising administering the composition according to claim 1, said method comprising applying the composition on the scalp in a circular motion at the hair root and leaving on said scalp for at least five minutes.

* * * * *